United States Patent [19]

Saenz Arroyo

[11] Patent Number: 4,787,887
[45] Date of Patent: Nov. 29, 1988

[54] VENTRICULAR BY-PASS VALVE FOR DRAINING THE CEPHALORACHIDIAN LIQUID IN THE HYDROCEPHALUS

[75] Inventor: Luis Saenz Arroyo, Mexico City, Mexico

[73] Assignee: Biomedica Mexicana, S.A., Mexico City, Mexico

[21] Appl. No.: 57,724

[22] Filed: Jun. 2, 1987

Related U.S. Application Data

[63] Continuation of Ser. No. 741,367, Jun. 5, 1985, abandoned.

[30] Foreign Application Priority Data

Aug. 16, 1984 [FI] Finland .................................. 843252

[51] Int. Cl.⁴ .............................................. A61N 5/00
[52] U.S. Cl. .................................... 604/9; 604/247
[58] Field of Search ................ 604/9, 27, 33, 247, 604/249, 323, 350

[56] References Cited

U.S. PATENT DOCUMENTS

| | | | |
|---|---|---|---|
| 3,111,125 | 11/1961 | Schulte | 604/9 |
| 3,288,142 | 11/1966 | Hakim | 604/9 |
| 4,310,017 | 1/1982 | Raines | 604/247 |
| 4,354,492 | 10/1982 | McPhee | 604/247 |
| 4,468,224 | 8/1984 | Enzmann et al. | 605/247 |

Primary Examiner—Stephen C. Pellegrino
Attorney, Agent, or Firm—Ladas & Parry

[57] ABSTRACT

The invention is a ventricular by-pass device for draining the cephalorachidian liquid in the hydrocephalus. It consists of a check valve device which obstructs the brain suction orifice.

4 Claims, 2 Drawing Sheets

A-A

VENTRICULAR BY-PASS VALVE FOR DRAINING THE CEPHALORACHIDIAN LIQUID IN THE HYDROCEPHALUS

This is a continuation of co-pending application Ser. No. 741,367 filed on June 5, 1985, now abandoned.

BACKGROUND OF THE INVENTION

This invention relates to a ventricular by-pass valve which is known in several countries and was originally designed in the United States of America in the year 1958. In the United States it is known as the Pudenz valve, in Japan as the Fuji valve, etc.

In the original design, adopted by several countries, the valve consists of a biconvex structure having an intermedium veil, these three elements being made from a silicon rubber elastomeric material having a connection toward the brain and another connection toward the heart or peritoneum. This mechanism ensures the outflow of cephalorachidian liquid when it has been retained in the brain causing hydrocephalus. The arrangement of the different elements comprised by the valve causes it to function as a one-way pump too, which, through outside handling, produces faster ejection of the brain liquid. Experience has demonstrated that notwithstanding its excellent operating characteristics, this design is capable of eventual collapse by the unpredictable action of forces originated by the elastomer itself and by negative pressure produced after the impelling force. This phenomenon can cause problems in the operation of the equipment.

Although the design has been known for more than 25 years and has had the preference of some investigators, many types of more complex and expensive by-pass valves were designed all over the world, but these are more easily obstructed.

Through the accumulated and published experience it was known that the old "Pudenz" design continued to be preferred, but keeping in greater or lesser degree, as an undesirable eventuality, the collapsing failure during use. Many investigators tried, by using different designs on the inclusion of various devices, to avoid the eventual collapse in the original design, but giving up other advantages of the original valve and exposing the valve to damage of its inner structure when carrying out punctures that are usually made to obtain samples of the cephalorachidian liquid. This background constitutes the basis for the studies which led to the present invention.

OBJECT OF THE INVENTION

The present invention relates to improvements in the conventional pumping equipments (Pudenz type), which are a part of the drainage systems of the cephalorachidian liquid used for hydrocephalus treatment. The object of these improvements is to avoid the pump from collapsing during the digital compression that the patient or the doctor performs to accelerate the drainage or to displace coagulums.

The invention will be explained with reference to the enclosed drawings which illustrate the invention as follows.

DETAILED DESCRIPTION OF THE INVENTION

Figure 1:
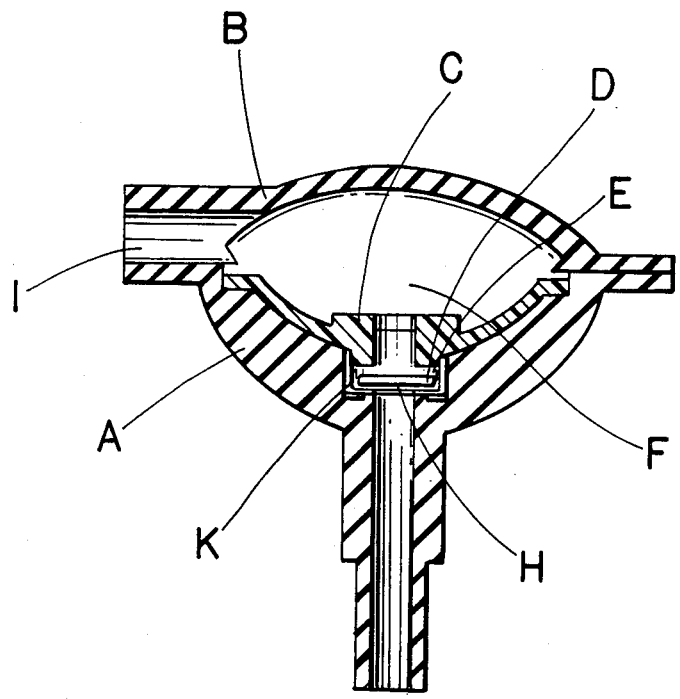
FIG. 1 is an arrangement of the four pieces comprised by the present invention after the equipment is assembled and adhered with appropriate materials.

As shown in FIG. 1, at the middle of the lower portion where piece A joins piece C, is the cylindrical chamber (E) in which diaphragm (D) is located. In that chamber E, said diaphragm reciprocates, passively actuated by pressure changes. If the pressure is greater in chamber F formed by domes (A and B), the diaphragm obstructs the central orifice where the brain drain drains, causing the liquid to flow through the drain going to the heart or to the peritoneum (I). On the contrary if the pressure is lower in chamber (F) the diaphragm rises and allows the liquid to flow towards the chamber. The orifice of device C cannot be obstructed by the diaphragm because device C has tooth-like projections that allow the flow of liquid and avoid the obstruction of the diaphragm. These conditions allow the device to operate as a reciprocating pump, sucking the cephalorachidian liquid from the brain and pumping it to the heart or to the peritoneum.

The design as a whole forms a geometrical figure similar to a flat sphere having a flange on the position corresponding to the equator (See FIG. 1). It consists of four pieces:

(A) A lower dome or base corresponding to the brain side manufactured from silicon rubber or other compatible material (see FIG. 1, letter A).

(B) An impelling top dome corresponding to the opposite side manufactured also from the same material (See FIG. 1, letter B).

Figure 2:
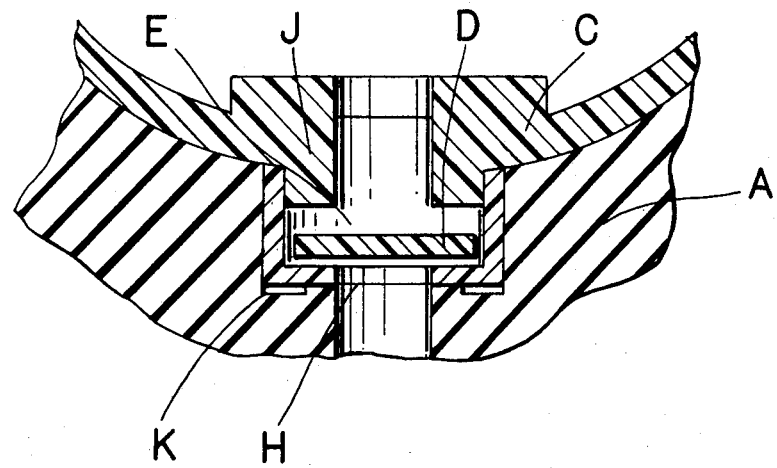
FIG. 2 is an enlarged sectional view of the device showing the internal configuration of the devices of the invention.
Figure 3:
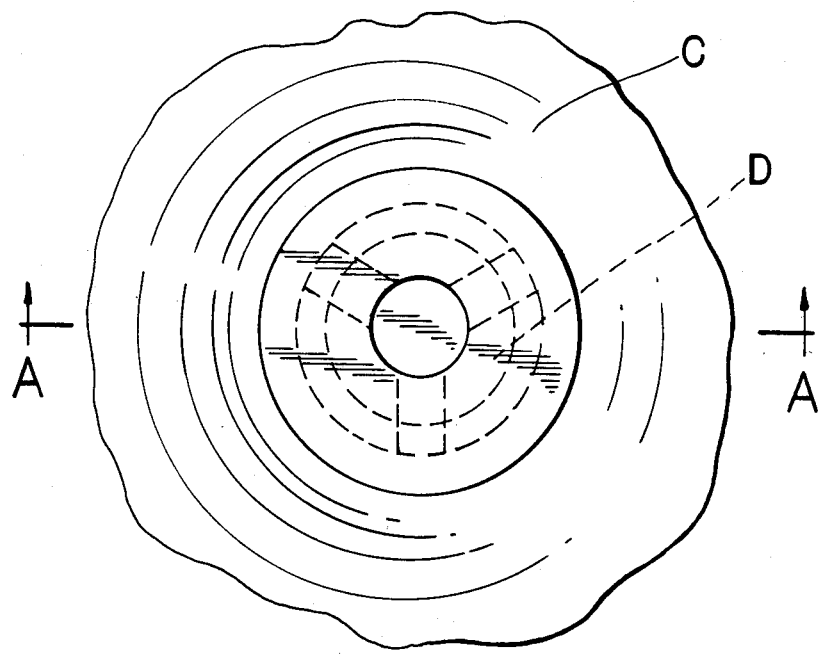
FIG. 3 illustrates an enlarged sectional side view of the device showing in detail the arrangement of the elements of the invention.

(C) A circular-contour cup-shaped concave figure manufactured of a rigid plastic or any other material of similar consistency having at its lower middle portion an orifice surrounded by three teeth projecting downward. This portion assembles with another cylindrical chamber in the form of an empty cartridge which has an orifice in its base. (See FIGS. 1 and 2, letter K.)

(D) A small diaphragm made of a rigid plastic material or any other material which operates as the element that obstructs the orifice during the impelling force. (See FIG. 1, letter D). It is located in the cylindrical chamber described in the previous paragraph.

The object of this invention is to avoid the use of a mechanism formed by a veil or intermediate film of a resilient material which operates as the check valve during the impelling force at the pumping time; this system which has been traditionally used causes, as previously mentioned, certain anomalous operations when in use, for instance, it causes the impelling dome, which is also manufactured from a resilient material, when inverted under pressure to lie physically on the elastomeric film which acts as a check valve. This causes the closing of the suction orifice for the cephalorachidian liquid, thus causing the impellent dome B not to return to its original form due to the vacuum originated between this inverted dome B and the base of the pump, causing a suctioning effect.

Although the dome collapse can be corrected in certain cases by itself due to the resilient proprieties of the dome, this correction is done progressively but slowly. Sometimes it is necessary to inject a sterile liquid into the pump to bring it to its original form. Although this anomaly is caused only by abnormal pressures during pumping, it interferes with the operation, with the resulting problems in the original design.

In order to eliminate this sucking phenomenon which causes the collapse of the pump, the following device, which is the object of this patent application, has been developed.

All pump types have an impelling mechanism and a check valve.

In the present invention the check valve location and the design have been modified. This modification which is an improvement to the conventional design, avoids, as will be seen later, the collapse of the dome and protects the check valve against damages caused by needle punctures used sometimes to obtain cephalorachidian liquid samples.

DESCRIPTION OF THE PREFERRED EMBODIMENT

On the dome base A a rigid material cup is located; and on the lower and middle portion this cup ends in a chamber in the form of an empty cylindrical cartridge with a through orifice which communicates with the upper chamber. At the lower portion this chamber, which has an inner diaphragm, communicates directly with the brain drain.

The check valve which is the subject matter of this invention, is located and protected by the rigid cup. When parts A and C are assembled together, a cylindrical chamber is integrated where the diaphragm is located. In that same structure the described through orifice is located and three teeth are projected downwards therefrom which are located around said orifice, positioned at 120° from each other. These teeth do not allow the diaphragm to obstruct the orifice that connects chamber C and F of FIG. 1, thus allowing the free flow of liquid between both chambers. As it can be seen from the above the cylindrical chamber having the check valve is located at the cavity formed at the dome base while the upper portion is formed by the lower and middle section of the rigid cup. At the lower portion of this cavity there is the orifice which communicates to the brain drain and to a seat for supporting the diaphragm.

This invention improves the operation of the conventional designs because it avoids the collapse of the impelling dome during operation, for it does not allow said dome to lie, when in an inverted position, on the check valve which does not exist anymore. The diaphragm is protected in a separate chamber; the rigid cup separates it from the dome, thus avoiding the pump to collapse, as previously described.

On the other hand the check valve is not damaged by hypodermic needle punctures (which is a frequent operation in patients using these valves) due to the protection of the rigid material cup C.

What we claim is the following:

1. A ventricular by-pass device for draining the cephalorachidian liquid in the hydrocephalus, comprising a check device which obstructs a brain suction orifice carved at the Calvarium, during the impelling force and allows the flow of cephalorachidian liquid during suction, said device comprising a one-way check valve of the wafer type independently located in a cylindrical chamber located at a cavity formed in a dome base and protected by a rigid cup located on the dome base and housed on a bone trepanation, said cup having at its lower middle portion an orifice surrounded by three teeth projecting downward and being positioned at 120° from each other around said orifice said lower middle portion assembled with a chamber having the form of an empty cylindrical cartridge with a through orifice communicating with an upper chamber, the lower portion of said cylindrical chamber, which has an inner diaphragm, is in direct communication with the brain, said cylindrical chamber carrying the check valve at the cavity formed at the dome base, said lower chamber in direct communication with the brain having a seat for supporting the check valve.

2. The ventricular by-pass device of claim 1, wherein said check valve is in a form of a cone.

3. The ventricular by-pass device of claim 1 wherein said check valve is in the form of a sphere.

4. A valve for draining cephalorachidian fluid in hydrocephalus comprising:
   a flexible upper dome
   a flexible lower dome, said upper and lower domes forming a flat sphere,
   a circular contour cup shaped element formed of material which is more rigid than said upper and lower domes and having a cylindrical chamber at a central portion thereof, said element being assembled inside of said lower dome with said cup-shaped portion in contact with walls of said lower dome and said chamber portion located in a chamber-receiving portion of said lower dome;
   a flat diaphragm formed of material which is more rigid than said domes, said flat diaphragm being disposed in the cylindrical chamber, and operating as a check valve;
   a plurality of teeth in said chamber projecting in an outward direction from interior of said sphere and being positioned around an orifice located at the lower middle portion of the cup;
   inlet means coupled to said chamber via an orifice in a wall of said chamber;
   outlet means coupled to said interior of said sphere.

* * * * *